(12) United States Patent
Park et al.

(10) Patent No.: US 9,476,896 B2
(45) Date of Patent: Oct. 25, 2016

(54) SAMPLE INSPECTION APPARATUS AND CONTROL METHOD THEREOF

(71) Applicant: SAMSUNG ELECTRONICS CO., LTD., Suwon-si (KR)

(72) Inventors: Jin Soo Park, Suwon-si (KR); Soo Hong Kim, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 10 days.

(21) Appl. No.: 14/528,118

(22) Filed: Oct. 30, 2014

(65) Prior Publication Data

US 2015/0212052 A1 Jul. 30, 2015

Related U.S. Application Data

(60) Provisional application No. 61/978,395, filed on Apr. 11, 2014.

(30) Foreign Application Priority Data

Jan. 29, 2014 (KR) ........................ 10-2014-0011406

(51) Int. Cl.
*G01N 1/00* (2006.01)
*G01N 35/10* (2006.01)
*G01N 35/00* (2006.01)
*B01L 3/00* (2006.01)
*B01L 9/00* (2006.01)

(52) U.S. Cl.
CPC ........... *G01N 35/10* (2013.01); *B01L 3/50273* (2013.01); *B01L 9/527* (2013.01); *G01N 35/00029* (2013.01); *B01L 2300/0816* (2013.01); *B01L 2400/0481* (2013.01); *G01N 2035/00128* (2013.01); *G01N 2035/1027* (2013.01)

(58) Field of Classification Search
CPC ........ G01N 1/28; G01N 21/35; G01N 29/02; G01N 30/28; G01N 33/48785; G01N 35/00613; G01N 35/1011; G01N 35/1095; G01N 9/04
USPC ...................................... 73/864.83
See application file for complete search history.

(56) References Cited

U.S. PATENT DOCUMENTS

2011/0195490 A1* 8/2011 Kang .................. G01N 33/492
435/287.1

\* cited by examiner

*Primary Examiner* — Harshad R Patel
*Assistant Examiner* — Brandi Hopkins
(74) *Attorney, Agent, or Firm* — Sughrue Mion, PLLC

(57) ABSTRACT

Disclosed are a sample inspection apparatus and a control method thereof. The sample inspection apparatus includes a housing, a cartridge insertable into one side of the housing and configured to receive a sample, a pressing member disposed within the housing and configured to press the cartridge to inspect the sample, a fluid storage part configured to transfer a fluid to the pressing member so that the pressing member presses the cartridge, and a fluid supply part configured to supply the fluid into the fluid storage part.

20 Claims, 7 Drawing Sheets

SAMPLE INSPECTION APPARATUS AND CONTROL METHOD THEREOF

CROSS-REFERENCE TO RELATED APPLICATIONS

This application claims priority from Korean Patent Application No. 10-2014-0011406, filed on Jan. 29, 2014 in the Korean Intellectual Property Office and claims the benefit of U.S. Patent Application No. 61/978,395, filed on Apr. 11, 2014 in the United States Patent and Trademark Office, the disclosures of which are incorporated herein by reference.

BACKGROUND

1. Field

Apparatuses and methods consistent with exemplary embodiments relate to a sample inspection apparatus and a control method thereof, and more particularly, to a sample inspection apparatus which has an improved structure to reduce a size thereof, and a control method thereof.

2. Description of the Related Art

An apparatus and method of analyzing a fluid sample is needed in various fields such as environment monitoring, food inspection, and medical diagnosis. Conventionally, in order to perform an inspection by a predetermined protocol, a skilled experimenter manually carries out various processes such as reagent injecting, mixing, separating and moving, reacting and centrifugal separating over several times, and these processes often cause errors in inspection results.

In order to address this problem, there has been developed a small and automatic apparatus for rapidly analyzing an inspection material.

In order to detect the inspection material contained in the sample, a characteristic reaction between the inspection material and a specific material may be used. And optical data of the fluid sample is measured using an optical sensor, and the concentration of the inspection material is obtained from a size or a changed amount of the measured optical data.

In the sample inspection, a cartridge configured to receive the sample is pressed by a pressing member, the sample is moved, and the inspection is performed. To this end, a device for moving the pressing member toward the cartridge is needed, and due to such a device, it is difficult to reduce a size of the sample inspection apparatus.

SUMMARY

Therefore, according to one or more exemplary embodiments, a sample inspection apparatus is provided which may move a pressing member to apply a pressure to a cartridge and which has an improved structure to reduce a size thereof, and a control method thereof.

Additional exemplary aspects and advantages of exemplary embodiments will be set forth in part in the description which follows and, in part, will be obvious from the description, or may be learned by practice.

In accordance with an aspect of an exemplary embodiment, a sample inspection apparatus includes a housing, a cartridge insertable into one side of the housing and configured to receive a sample, a pressing member disposed in the housing and configured to press the cartridge to inspect the sample, a fluid storage part configured to transfer a fluid to the pressing member so that the pressing member presses the cartridge, and a fluid supply part configured to supply the fluid into the fluid storage part.

A valve may be disposed in communication with passages connected to the pressing member, the fluid storage part, and the fluid supply part, to open and close each passage.

The valve may be a 3-way valve which is rotatable to open and close each port thereof.

The sample inspection apparatus may further include a control part configured to determine whether the pressing member is normally located at the cartridge and to control an operation of the fluid supply part and an opening and closing of the valve.

The control part may stop the operation of the fluid supply part when the pressing member is normally located at the cartridge, and control the fluid to be moved from the fluid storage part to the pressing member.

The fluid supply part may be an air pump configured to inject air.

The fluid storage part may be a metering chamber configured to receive a fixed amount of fluid.

The fluid supply part may be a manual pump which is grasped and manually operated.

In accordance with an aspect of another exemplary embodiment, a sample inspection apparatus includes a housing, a cartridge insertable into one side of the housing and configured to receive a sample, a pressing member disposed in the housing and configured to press the cartridge to inspect the sample, a valve configured to open and close a communication port communicating with the pressing member, and a control part configured to control an opening and closing of the valve so that a fixed amount of fluid is introduced into the pressing member, wherein the pressing member applies a pressure to the cartridge due to the fluid introduced to the pressing member.

The sample inspection apparatus may further include a fluid storage part configured to transfer the fluid to the pressing member so that the pressing member presses the cartridge.

The sample inspection apparatus may further include a fluid supply part configured to supply the fluid to the fluid storage part.

The valve may be a 3-way valve including communication ports which are respectively in communication with the pressing member, the fluid storage part, and the fluid supply part.

When the fluid is moved from the fluid supply part to the fluid storage part, the valve may be located at a first position, and when the fluid is moved from the fluid storage part to the pressing member, the valve may be rotated and located at a second position.

The fluid storage part may be a metering chamber configured to receive a fixed amount of fluid.

The fluid supply part may be an air pump configured to inject air.

The fluid supply part may be a manual pump which is grasped and manually operated.

In accordance with an aspect of another exemplary embodiment, a control method of a sample inspection apparatus includes moving a fluid from a fluid supply part to a fluid storage part, moving the fluid stored in the fluid storage part to a pressing member, and pressing a cartridge by the pressing member using the fluid moved from the fluid storage part, and performing an inspection of a sample in the cartridge.

When the fluid stored in the fluid storage part is moved to the pressing member, the fluid supply part may be stopped.

The moving of the fluid from the fluid supply part to the fluid storage part, and the moving of the fluid from the fluid storage part to the pressing member may include converting a flow direction of the fluid by rotation of a valve.

When fluid is moved from the fluid storage part to the pressing member, a control part may determine whether the pressing member is normally located on the cartridge.

BRIEF DESCRIPTION OF THE DRAWINGS

These and/or other exemplary aspects and advantages will become apparent and more readily appreciated from the following description of exemplary embodiments, taken in conjunction with the accompanying drawings in which.

DETAILED DESCRIPTION

Figure 1:
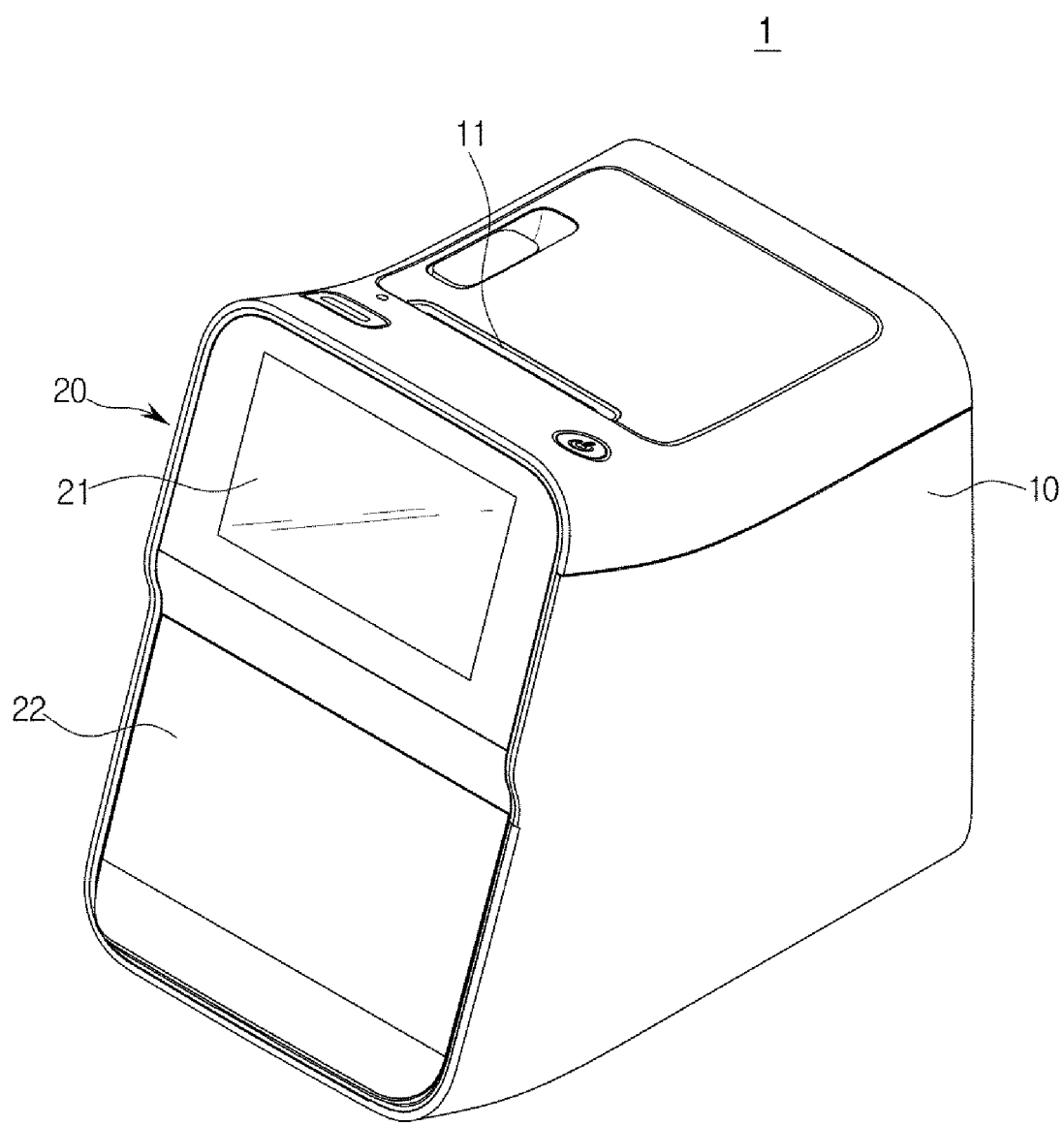
FIG. 1 is a view illustrating an exterior of a sample inspection apparatus in accordance with an exemplary embodiment.

Reference will now be made in detail to exemplary embodiments, examples of which are illustrated in the accompanying drawings, wherein like reference numerals refer to like elements throughout.

Figure 2:
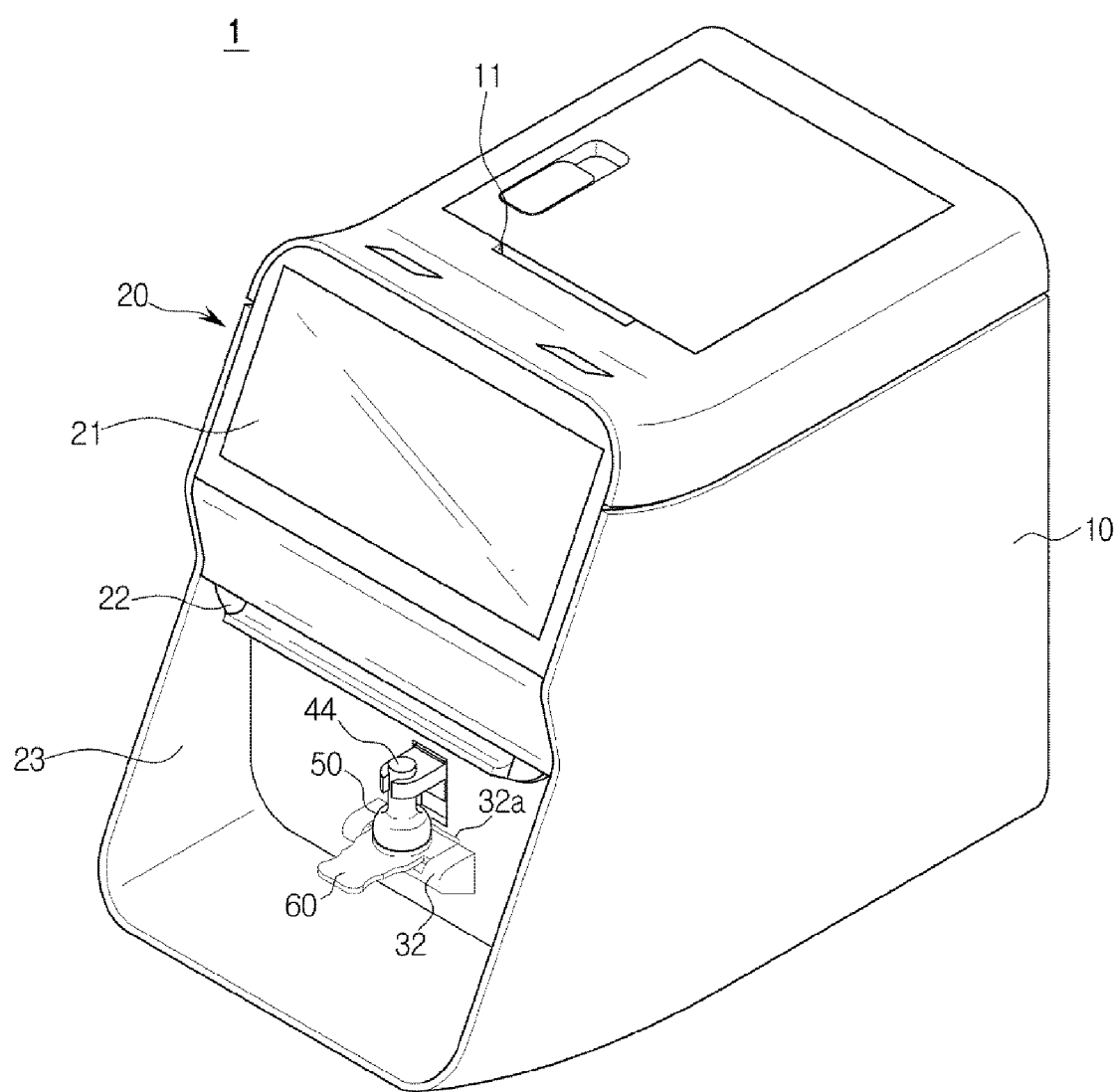
FIG. 2 is a view illustrating an opened state of a door of the sample inspection apparatus in accordance with an exemplary embodiment.

FIG. 1 is a view illustrating an exterior of a sample inspection apparatus in accordance with an exemplary embodiment, and FIG. 2 is a view illustrating an opened state of a door of the sample inspection apparatus in accordance with an exemplary embodiment.

As illustrated in FIGS. 1 and 2, a sample inspection apparatus 1 according to one embodiment of the present invention includes a housing 10, defining an interior space, and a door module 20 provided at a front side of the housing 10.

The door module 20 may include a display part 21, a door 22, and a door frame 23. The display part 21 and the door 22 may be disposed at a front side of the door frame 23. The display part 21 may be disposed above the door 22. The door 22 is slidable, such that the door 22 may be located at a rear side of the display part 21 when the door 22 has been slid into an open position.

The display part 21 may display information of analysis contents of a sample, states of sample analysis operation, or the like. The door frame 23 may have an installation member 32 into which a cartridge 60 configured to receive a fluid sample may be installed. A user may open the door 22 by sliding it upward, may install the cartridge 60 at the installation member 32, slide the door 22 downward and close the door 22, and then perform the analysis operation.

A fluid sample is injected into the cartridge 60 and reacts with a reagent at an inspection part (not shown). The cartridge 60 is then inserted into the installation member 32, and a pressing member 50 presses the cartridge 60 so that the fluid sample in the cartridge 60 is introduced into the inspection part (not shown).

Further, an output part 11, configured to output inspection results as a printed document, may be further provided separately from the display part 21.

Figure 3:
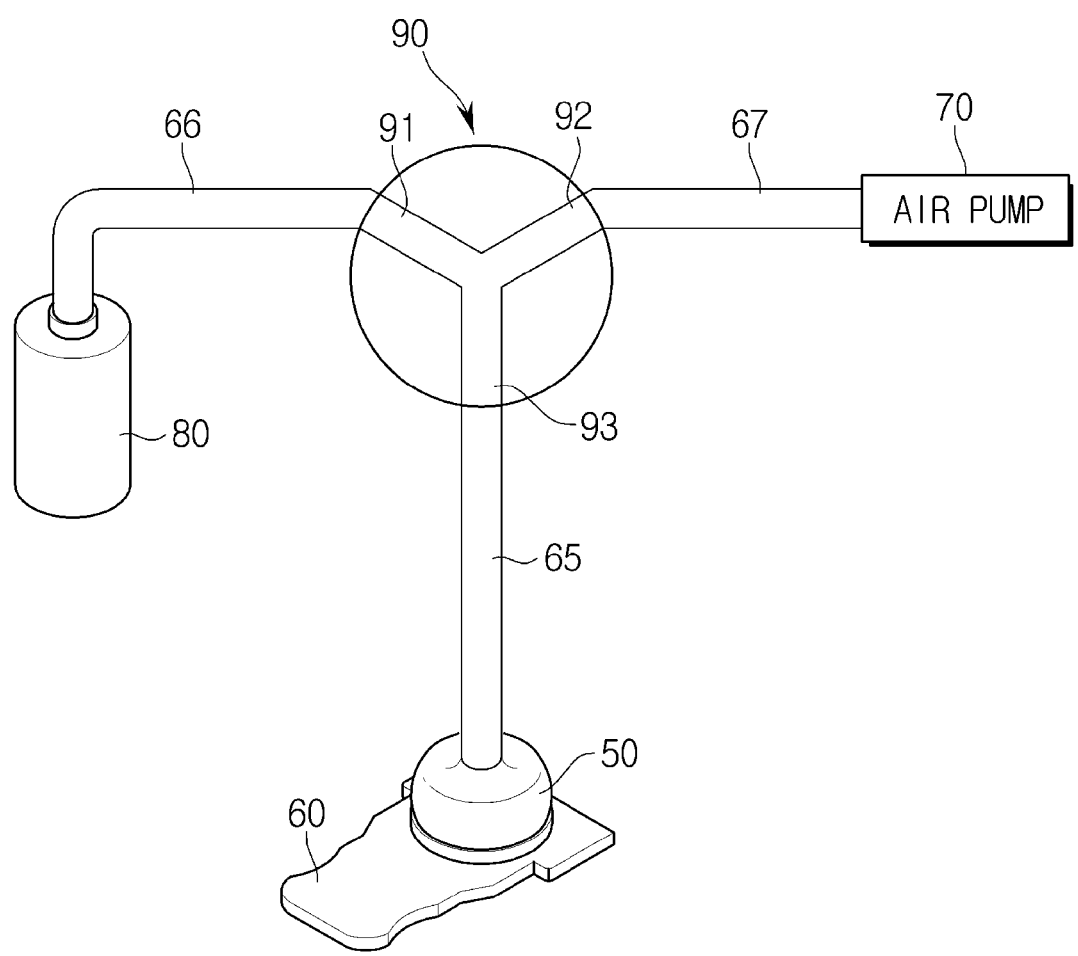
FIG. 3 is a view schematically illustrating a principle of driving a pressing member of the sample inspection apparatus in accordance with an exemplary embodiment.
Figure 4:
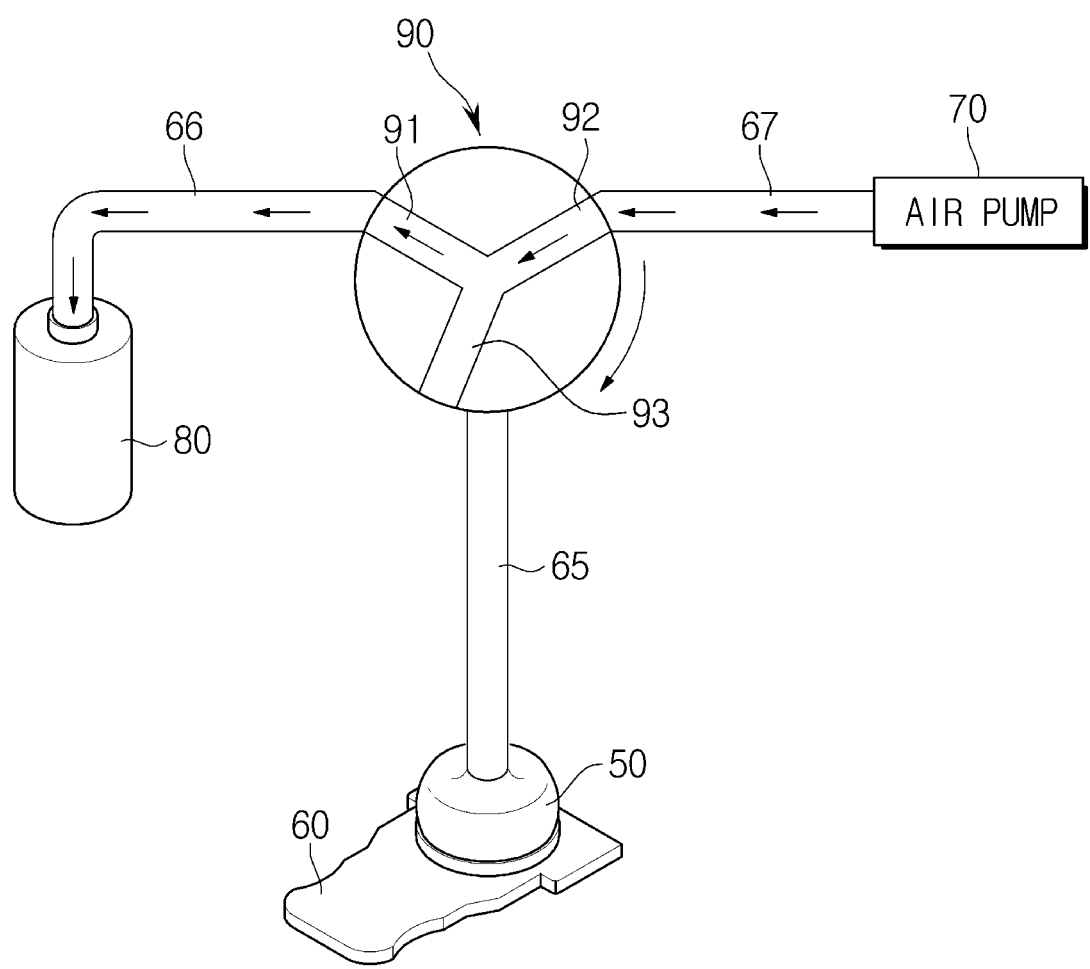
FIGS. 4 and 5 are views illustrating a fluid flow in the sample inspection apparatus in accordance with n exemplary embodiment.
Figure 5:
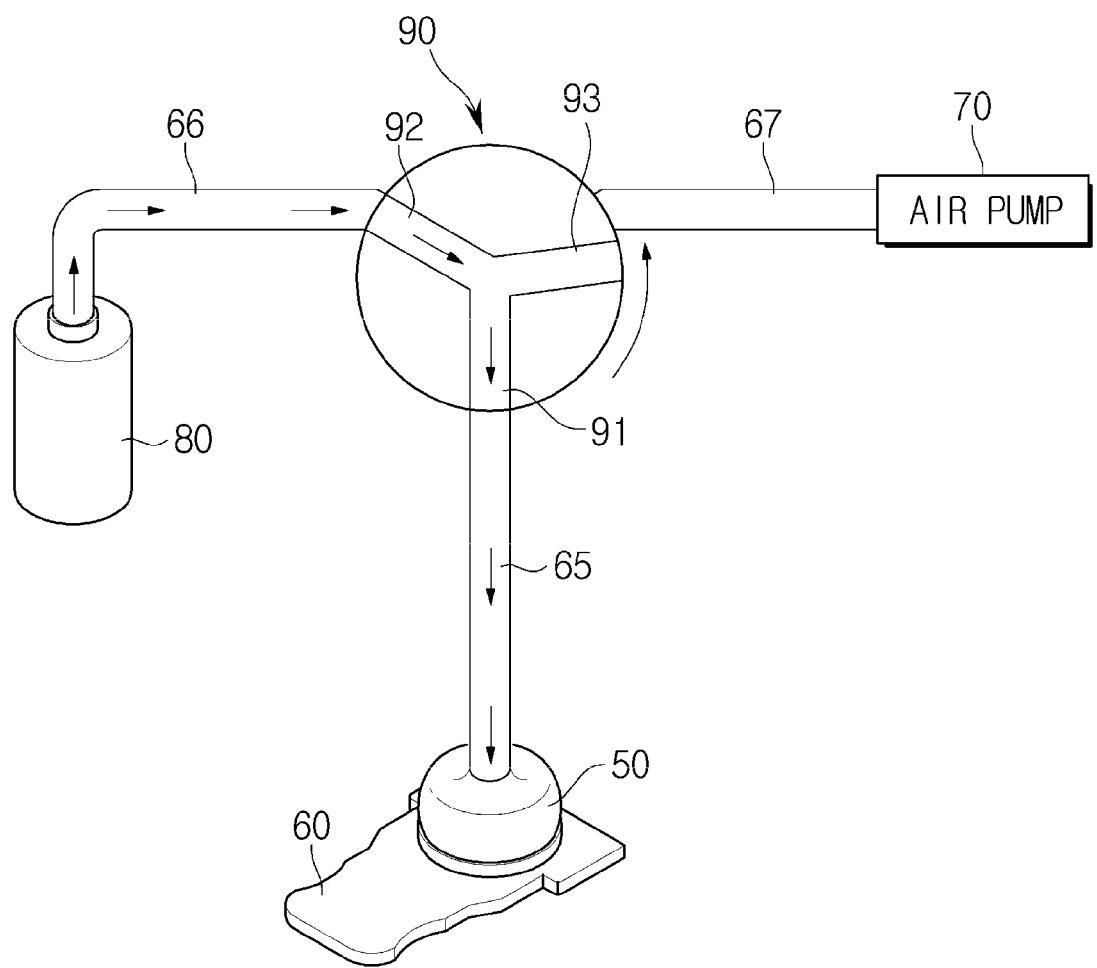

FIG. 3 is a view schematically illustrating a principle of driving the pressing member of the sample inspection apparatus in accordance with an exemplary embodiment, and FIGS. 4 and 5 are views illustrating a fluid flow in the sample inspection apparatus in accordance with an exemplary embodiment.

As illustrated in FIGS. 3 to 5, in order to drive the pressing member 50 toward the cartridge 60, a fluid storage part 80 and a fluid supply part 70 may be used. An air pump illustrated in the drawing is an example of the fluid supply part 70. A membrane pump may be used for the air pump used as the fluid supply part 70. In the membrane pump, a check valve is opened and closed by an internal pressure difference generated by movement of a membrane when the membrane is vibrated up and down, and thus the fluid is moved. However, this example is not limiting, and any of various types of pumps may be used.

The fluid storage part 80 may be a metering chamber which may receive the fluid. Therefore, a predetermined amount of the fluid may be received in the fluid storage part 80. That is, the fluid is moved toward the pressing member 50, and the pressing member 50 presses the cartridge 60. According to an exemplary embodiment air is used, but this is not limiting.

A valve 90 may be disposed among the fluid storage part 80, the fluid supply part 70, and the pressing member 50. The valve 90 may be a 3-way valve including a first communication port 91, a second communication port 92, and a third communication port 93. Each communication part 91, 92, and 93 may be in communication with the fluid storage part 80, the fluid supply part 70, and the pressing member 50. The pressing member 50 may be provided to be connected with a first pipe 65 in communication with one communication port of the 3-way valve 90. A pipe connecting the fluid storage part 80 and the valve 90 is defined as a second pipe 66, and a pipe connecting the air pump 70 and the valve 90 is defined as a third pipe 67.

A control part (not shown) may control opening and closing of the valve 90. Therefore, the control part (not shown) determines whether the pressing member 50 is normally located at the cartridge 60, and stops an operation of the fluid supply part 70 or controls the opening and closing of the valve 90. When the pressing member 50 is normally located at the cartridge 60, the control part (not shown) stops the operation of the fluid supply part 70 and controls the fluid to be moved from the fluid storage part 80 to the pressing member 50. To this end, rotation of the valve 90 may be used, and this will be described later.

The pressing member 50 may include a body portion configured to press the cartridge 60, and the first pipe 65 which is in communication with one communication port of the valve 90. The body portion and the first pipe 65 may integrally formed, but the device is not limited thereto. The body portion and the first pipe 65 may be separately provided, and the first pipe may be inserted into the pressing member. The first pipe 65 may be coupled to a holder 44 of the housing 10. The pressing member 50 may be formed of a flexible material. As an example, the pressing member 50 may be formed of silicone, urethane, or rubber, but is not limited thereto. And the pressing member 50 may be formed of a deformable material.

FIG. 4 illustrates a process in which the fluid is moved from the fluid supply part to the fluid storage part, and FIG. 5 illustrates a process in which the fluid is moved from the fluid storage part to the pressing member.

The fluid is firstly moved from the fluid supply part 70 to the fluid storage part 80. At this time, the valve 90 is positioned so that the first communication port 91 is in communication with the fluid storage part 80, and the second communication port 92 is in communication with the fluid supply part 70. The third communication port 93 is positioned toward the pressing member 50, but not in communication with the pressing member 50 so that the fluid is not moved to the pressing member 50.

Then, the fluid stored in the fluid storage part 80 is moved to the pressing member 50. At this time, the valve 90 is rotated so that the first communication port 91 is in communication with the pressing member 50, and the second communication port 92 is in communication with the fluid storage part 80. The third communication port 93 is positioned toward the fluid supply part 70, but not in communication with the fluid supply part 70 to prevent the fluid from flowing backward.

That is, when the fluid is moved from the fluid supply part 70 to the fluid storage part 80, the valve 90 is positioned in a first position, as illustrated in FIG. 4. Further, when the fluid is moved from the fluid storage part 80 to the pressing member 50, the valve 90 is rotated and positioned in a second position, as illustrated in FIG. 5.

Since the fluid is firstly received in the fluid storage part 80 and then moved to the pressing member 50, a fixed amount of fluid may be moved to the pressing member 50, and thus the pressing member 50 may apply a constant pressure to the cartridge 60. Further, when the fluid is directly moved from the fluid supply part 70 to the pressing member 50, vibration may occur due to the operation of the fluid supply part 70, and this may be prevented.

Since the fluid storage part 80 is the metering chamber, an amount of fluid transferred to the pressing member 50 may be adjusted, and thus a pressing level may be also controlled. Further, a pressing time may be controlled according to a pressure supply level of the fluid supply part 70.

Figure 6:
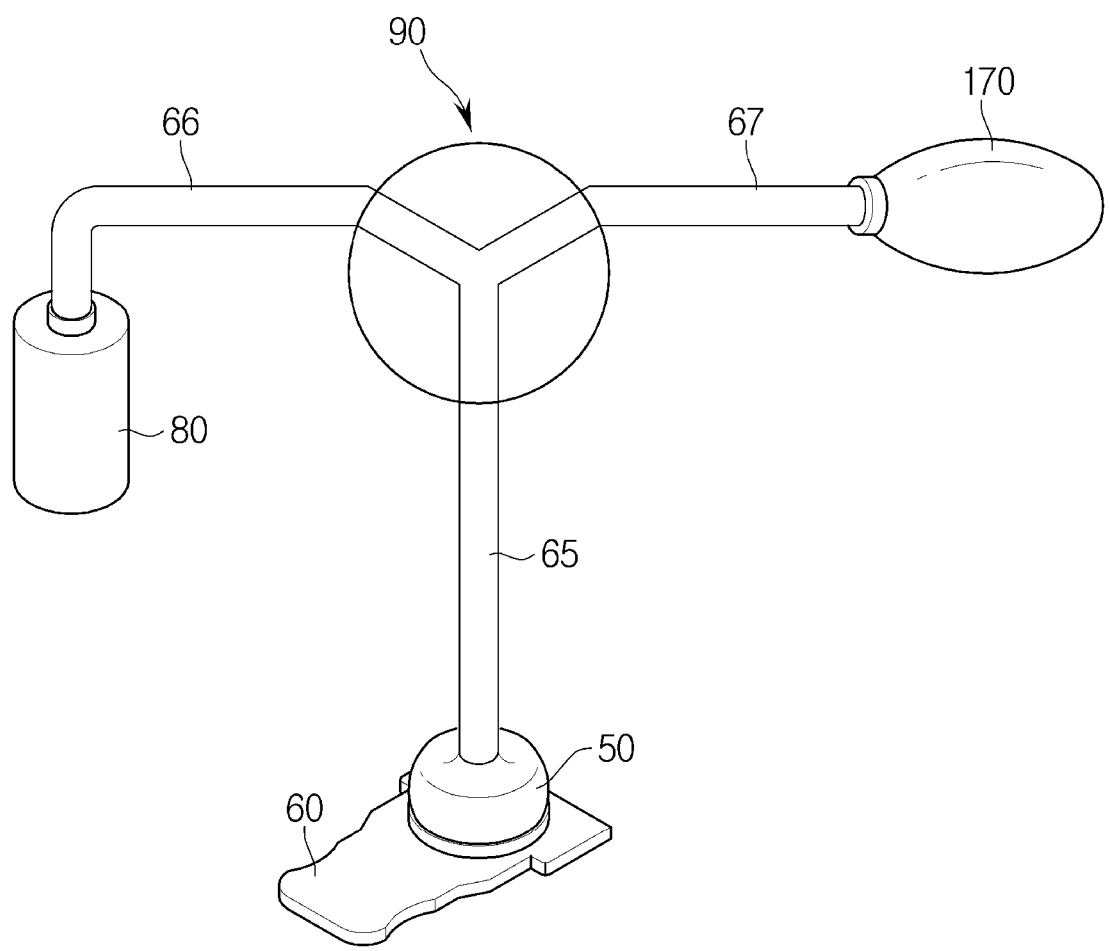
FIG. 6 is a view schematically illustrating a principle of driving a pressing member of a sample inspection apparatus in accordance with an exemplary embodiment.

FIG. 6 is a view schematically illustrating a principle of driving a pressing member of a sample inspection apparatus according to an exemplary embodiment.

As illustrated in FIG. 6, a fluid supply part 170 may be a manual pump which may be grasped and manually operated. If the user manually presses the manual pump and supplies air to the fluid storage part 80, air in the fluid storage part 80 is moved to the pressing member 50.

At this time, the valve 90 may be the 3-way valve. The valve 90 may rotate to close a communication port connected to the fluid supply part 170 or close a communication port connected to the pressing member 50.

Further, a check valve (not shown) may be additionally provided between the fluid supply part 170 and the valve 90. This is to prevent the fluid from flowing backward, i.e., to enable an air flow generated by a grasping motion of the user to move in a direction away from the fluid supply part 170, thereby preventing the air flow from flowing backward into the fluid supply part 170.

Figure 7:
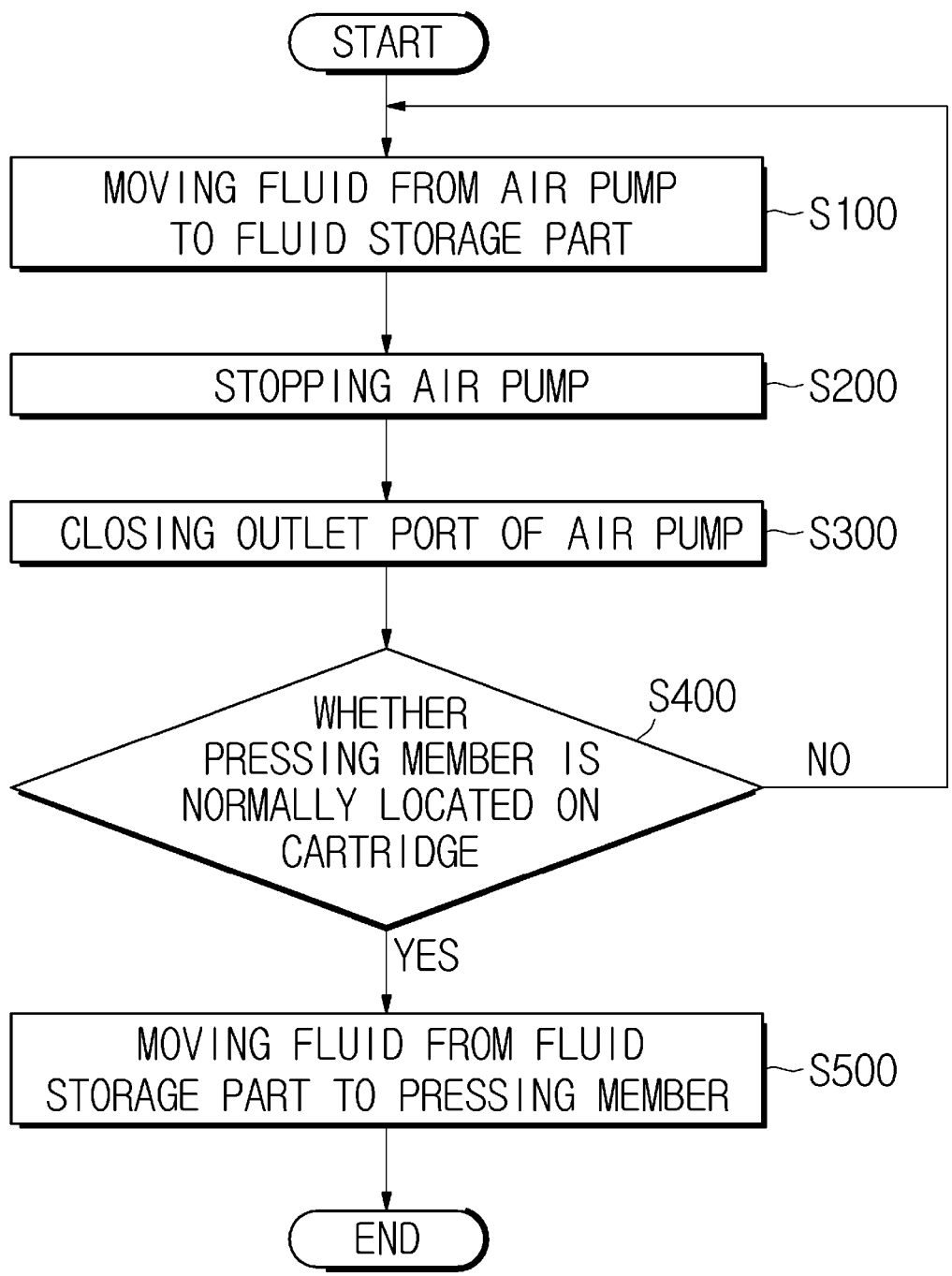
FIG. 7 is a flowchart illustrating a control method of the sample inspection apparatus in accordance with an exemplary embodiment.

FIG. 7 is a flowchart illustrating a control method of the sample inspection apparatus in accordance with an exemplary embodiment.

As illustrated in FIG. 7, a control method of the sample inspection apparatus 1 according to an exemplary embodiment includes (S100) moving the fluid from the fluid supply part to the fluid storage part, (S500) moving the fluid stored in the fluid storage part to the pressing member, and the pressing member pressing the cartridge by the fluid moved from the fluid storage part. Thereby, an inspection of the sample in the cartridge is performed. Here, the fluid supply part may be the air pump.

When the fluid stored in the fluid storage part is moved to the pressing member (S500), the fluid supply part is stopped (S200). Further, the valve is rotated to close the communication port connected with the fluid supply part (S300). Therefore, the fluid of the fluid storage part is prevented from being moved to the fluid supply part, and also the fluid is prevented from being moved from the fluid supply part to the fluid storage part or the pressing member. Thus, only the predetermined amount of fluid metered in the fluid storage part is moved to the pressing member.

Further, when the fluid is moved from the fluid storage part to the pressing member (S500), it is possible to additionally determine whether the pressing member is normally located on the cartridge (S400). That is, when the pressing member is normally located on the cartridge, the fluid is moved from the fluid storage part to the pressing member, and when pressing member is not normally located on the cartridge, the fluid is moved from the fluid supply part to the fluid storage part.

According to an exemplary sample inspection apparatus, the sample inspection apparatus can have a small size by improving the structure of moving the pressing member.

Although a few embodiments have been shown and described, it would be appreciated by those skilled in the art that changes may be made in these embodiments without departing from the principles and spirit of the inventive concept, the scope of which is defined in the claims and their equivalents.

What is claimed is:

1. A sample inspection apparatus comprising:
   a housing;
   a cartridge insertable into one side of the housing and configured to receive a sample;
   a pressing member disposed within the housing and configured to press the cartridge upon application of a pressure thereto;
   a fluid storage part configured to transfer a fluid to the pressing member, thereby applying pressure to the pressing member causing the pressing member to press the cartridge; and
   a fluid supply part configured to supply the fluid into the fluid storage part.

2. The sample inspection apparatus according to claim 1, further comprising a valve in communication with the pressing member, the fluid storage part, and the fluid supply part, wherein the valve is configured to open and close each of a passage between the fluid supply part and the fluid storage part, a passage between the fluid storage part and the pressing member, and a passage between the fluid supply part and the pressing member.

3. The sample inspection apparatus according to claim 2, wherein the valve is a 3-way valve comprising three ports, wherein the valve is rotatable to open and close each of the three ports.

4. The sample inspection apparatus according to claim 2, further comprising a control part configured to determine whether the pressing member is correctly located at the cartridge and to control an operation of the fluid supply part and an opening and closing of the valve.

5. The sample inspection apparatus according to claim 4, wherein the control part stops the operation of the fluid supply part when the pressing member is correctly located at the cartridge, and controls the fluid to be moved from the fluid storage part to the pressing member.

6. The sample inspection apparatus according to claim 1, wherein the fluid supply part is an air pump.

7. The sample inspection apparatus according to claim 1, wherein the fluid storage part is a metering chamber configured to receive a fixed amount of fluid.

8. The sample inspection apparatus according to claim 1, wherein the fluid supply part is a manual pump.

9. A sample inspection apparatus comprising:
   a housing;
   a cartridge insertable into one side of the housing and configured to receive a sample;
   a pressing member disposed within the housing and configured to press the cartridge;
   a valve configured to open and close a passage in communication with the pressing member; and
   a control part configured to control an opening and a closing of the valve, thereby controlling the introduction of a fixed amount of into the pressing member, wherein an introduction of the fluid into the pressing member causes the pressing member to apply a pressure to the cartridge.

10. The sample inspection apparatus according to claim 9, further comprising a fluid storage part configured to transfer the fluid to the pressing member.

11. The sample inspection apparatus according to claim 10, further comprising a fluid supply part configured to supply the fluid to the fluid storage part.

12. The sample inspection apparatus according to claim 11, wherein the valve is a 3-way valve comprising three communication ports which are respectively in communication with the pressing member, the fluid storage part, and the fluid supply part.

13. The sample inspection apparatus according to claim 12, wherein, the valve is rotatable,
   when the fluid is moved from the fluid supply part to the fluid storage part, the valve is located at a first position, and
   when the fluid is moved from the fluid storage part to the pressing member, the valve is located at a second position.

14. The sample inspection apparatus according to claim 10, wherein the fluid storage part is a metering chamber configured to receive a fixed amount of fluid.

15. The sample inspection apparatus according to claim 11, wherein the fluid supply part is a manual pump.

16. The sample inspection apparatus according to claim 11, wherein the fluid supply part is an air pump.

17. A control method of a sample inspection apparatus, comprising:
   moving a fluid from a fluid supply part to a fluid storage part;
   moving fluid from the fluid storage part to a pressing member, thereby causing the pressing member to press a cartridge; and
   performing an inspection of a sample in the cartridge.

18. The method according to claim 17, further comprising stopping fluid flow from the fluid supply member, when moving fluid from the fluid storage part to the pressing member.

19. The method according to claim 18, wherein the moving fluid from the fluid supply part to the fluid storage part, and the moving fluid from the fluid storage part to the pressing member comprise converting a flow direction of fluid by rotating a valve.

20. The method according to claim 17, wherein, further comprising, prior to the moving fluid from the fluid storage part to the pressing member, a control part determining whether the pressing member is located on the cartridge.

* * * * *